United States Patent [19]

Clement et al.

[11] Patent Number: 4,961,631

[45] Date of Patent: Oct. 9, 1990

[54] NONLINEAR OPTICAL DEVICES FROM DERIVATIVES OF STILBENE

[75] Inventors: Robert A. Clement; Wilson Tam; Ying Wang, all of Wilmington, Del.

[73] Assignee: E. I Du Pont de Nemours and Company, Wilmington, Del.

[21] Appl. No.: 436,975

[22] Filed: Nov. 16, 1989

Related U.S. Application Data

[63] Continuation of Ser. No. 155,024, Feb. 11, 1988, abandoned.

[51] Int. Cl.$^5$ .......................... G02B 5/23; G03H 1/02; F21V 9/00
[52] U.S. Cl. ................................. 350/354; 252/582; 252/587; 252/600; 350/3.64
[58] Field of Search ............... 252/582, 583, 587, 589; 350/1.1, 350 R, 354, 3.64

[56] References Cited

U.S. PATENT DOCUMENTS

| | | | |
|---|---|---|---|
| 3,742,067 | 6/1973 | Steiger et al. | 260/613 |
| 3,767,289 | 10/1973 | Aviram et al. | 350/350 R |
| 4,859,876 | 8/1989 | Dirk et al. | 307/425 |

FOREIGN PATENT DOCUMENTS

| | | | |
|---|---|---|---|
| 315894 | 5/1989 | European Pat. Off. | 252/587 |
| 62-156628 | 7/1987 | Japan | 252/587 |
| 01173017 | 7/1989 | Japan | 252/587 |
| 1331228 | 9/1973 | United Kingdom | 252/587 |
| 2204053 | 11/1988 | United Kingdom | 252/587 |

OTHER PUBLICATIONS

Wang, Y. et al., Chem. Phys. Lett., 148 2,3 1988.
Ulman, A., J. Phys. Chem. 92, 2385, 1988.
Tam, W. et al., Proc. SPIE-Int. Soc. Opt. Eng., 971, 107, 1988.
Allen, S., New Scientist, p. 59, Jul. 1989.
Hall, S. R. et al., J. Crystal Growth, 79, 745, 1986.
Williams, D. J., Angew. Chem. Int. Ed. Engl., 23 690, 1984.
Tabei, H. et al., Appl. Phys. Lett. 50, 1855, 1987.
Coda, A.; J. Appl. Cryst. 9, 193, 1976.
March, J.; Advanced Organic Chemistry, 3rd., Wiley, New York, 1985.
Merckx, R., Bull. Chem. Soc. Belg. 58, 460, 1949.
Oudar, J. L., J. Chem. Phys. 67(2), 446, 1977.
Tweig, R. J.; Jan, K.; Organic Materials for Optical Second Harmonic Generation in "Nonlinear Optical Properties of Organic and Polymeric Materials", D. J. Williams, ed., ACS Symp. Ser. 223, ACS, Washington, D.C., 1983, Chapter 3.
Tweig, R. J., Organic Materials for Second Harmonic Generation, Report 1985, UCRL-15706.
Franken et al., Physical Review Letters, vol. 7, 118–119 (1961).
Coda et al., J. Appl. Cryst., vol. 9, 193 (1976).
Kurihara et al., J. Chem., Soc., Chem. Commun., 959–960 (1987).
Fouguey et al., J. Chem. Soc., Chem. Commun., 1424–1426 (1987).

*Primary Examiner*—John S. Maples
*Assistant Examiner*—Richard Treanor

[57] ABSTRACT

Certain derivatives of stilbene are capable of second harmonic generation when illuminated by coherent optical radiation.

8 Claims, No Drawings

NONLINEAR OPTICAL DEVICES FROM DERIVATIVES OF STILBENE

This application is a continuation of application Ser. No. 155,024, filed Feb. 11, 1988, now abandoned.

BACKGROUND OF THE INVENTION

1. Field of the Invention

This invention relates to nonlinear optical systems, and particularly to substituted stilbenes capable of second harmonic generation (SHG) and having other useful nonlinear optical and electro-optic properties.

2. Description of Related Art

The nonlinear optical response of a molecule can be described by the following expansion:

$$\mu = \mu_0 + \alpha E + \beta EE + \lambda EEE + \ldots$$

where $\mu$ is the induced dipole moment and $\mu_0$ is the permanent dipole moment of the molecule; $\alpha$, $\beta$, and $\lambda$ are the linear, second order and third order polarizabilities, respectively; E is the applied electric field. To describe an ensemble of molecules such as a crystal, the macroscopic relationship should be used:

$$P = P_0 + \chi^{(1)} E + \chi^{(2)} EE + \chi^{(3)} EEE + \ldots$$

where P is the induced polarization and $P_0$ is the permanent polarization; $\chi^{(1)}$, $\chi^{(2)}$ and $\chi^{(3)}$ are the linear, second order and third order susceptibility, respectively. Second order nonlinear optical phenomena such as second harmonic generation (SHG), sum and difference frequency generation, parametric processes and electro-optical effects all arise from the $\chi^{(2)}$ term. To have a large $\chi^{(2)}$, a molecule should both possess a large $\beta$ and crystallize in a noncentrosymmetric structure. Centrosymmetric crystals have vanishing $\chi^{(2)}$ and are therefore incapable of SHG.

Franken, et al., Physical Review Letters, Vol. 7, 118-119 (1961), disclose the observation of SHG upon the projection of a pulsed ruby laser beam through crystalline quartz. They observed the generation of the second harmonic of light, in which light of 6943 Å was converted to light of 3472 Å. The use of a laser remains the only practical way to generate an E large enough to be able to detect the SHG phenomenon.

Coda et al., J. Appl. Cryst., Vol. 9, 193 (1976), disclose SHG in a powder sample of 4-methoxy-4'-nitrostilbene.

Kurihara, et al., J. Chem. Soc., Chem. Commun., 959-960 (1987), disclose the synthesis of 4-methoxy-4'-nitrotolan (MNT) (i.e., 4-methoxy-4'-nitrodiphenylacetylene) and the use of MNT for SHG.

Fouquey, et al., J. Chem. Soc. Chem. Commun., 1424-6 (1987), disclose the preparation and crystal phase transition temperatures for several 4-amino-4'-nitrostilbene and 4-nitrodiphenylacetylene derivatives. Non-linear optical properties, including second harmonic generation, are noted for selected compounds.

Useful reviews of the art relating to nonlinear properties of organic materials are given in the following references: "Nonlinear Optical Properties of Organic and Polymeric Materials", D. J. Williams, ed., American Chemical Society, Washington, D.C. (1983); D. J. Williams, Angew. Chem., Int. Ed. Engl., Vol. 23, 690 (1984); "Nonlinear Optical Properties of Organic Molecules and Crystals", Vol. 2, D. S. Chemla, et al., ed., Associated Press, Orlando, Fla. (1987).

Although a large number of organic and inorganic materials capable of SHG have been found since Franken's discovery, an intense search continues. Through many years of research, it is now believed that an organic molecule having a conjugated $\pi$ electron system or a low-lying charge transfer excited state often has a large second order polarizability, $\beta$. Many molecules with large $\beta$ have been discovered based on these principles. However, many of these molecules have vanishing $\chi^{(2)}$ because of their unfavorable centrosymmetric crystal structures and therefore have no practical use. To this date, there is no absolute way of predicting whether a molecule can crystallize in a noncentrosymmetric structure.

SUMMARY OF THE INVENTION

The present invention provides a nonlinear optical device capable of second harmonic generation, comprising a nonlinear optical element and a source of coherent optical radiation, said nonlinear element comprising a crystalline compound which is crystallized in a noncentrosymmetric space group, said compound having the general formula

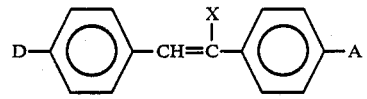

wherein A or D is $NO_2$ and, correspondingly,

D or A is selected from the group consisting of F, Cl, Br, I, CHO and OR where R is H, $C_1-C_{10}$ branched or unbranched alkyl, or $C_1-C_{10}$ branched or unbranched hydroxyalkyl, and X is selected from the group consisting of F, Cl, Br, I, CN, $C_1-C_4$ branched or unbranched alkyl.

The crystalline compounds are preferably chosen from the following:

1-cyano-1-(4-nitrophenyl)-2-(4-methoxyphenyl)ethylene;
1-cyano-1-(4-methoxyphenyl)-2-(4-nitrophenyl)ethylene;
1-methyl-1-(4-nitrophenyl)-2-(4-methoxyphenyl)ethylene;
1-cyano-1-(4-chlorophenyl)-2-(4-nitrophenyl)ethylene;
1-cyano-1-(4-bromophenyl)-2-(4-nitrophenyl)ethylene;
1-cyano-1-(4-nitrophenyl)-2-(4-bromophenyl)ethylene;
1-bromo-1-(4-nitrophenyl)-2-(4-bromophenyl)ethylene;
1-bromo-1-(4-nitrophenyl)-2-(4-methoxyphenyl)ethylene;

The invention also provides a method of generating second harmonic radiation using the nonlinear optical device. The invention also provides an electro-optic modulator using the nonlinear optical device.

DETAILED DESCRIPTION OF THE INVENTION

It has been found that certain derivatives of stilbene have not only large $\beta$, but also large $\chi^{(2)}$. These compounds have been shown to be capable of second harmonic generation.

Preparations for several of the stilbene derivatives used in the nonlinear optical devices of this invention have been disclosed: 1-cyano-1-(4-nitrophenyl)-2-(4-methoxyphenyl)ethylene by R. Merckx, Bull. Soc.

Belg., Vol. 58, 460-471 (1949); and 1-bromo-1-(4-nitrophenyl)-2-(4-bromophenyl)ethylene and 1-bromo-1-(4-nitrophenyl)-2-(4-methoxyphenyl)ethylene by A. Yamaguchi et al., Nippon Kagaku Kaishi, Vol. 11 2103-2107 (1972). Preparations for some of the stilbene derivatives that can be used in the nonlinear optical devices of this invention are given in the Examples.

It has also been found that the crystal structure of these stilbene derivatives can depend on the method used to obtain the crystals. Thus, as shown in the Table, the SHG efficiency for a given compound will depend on the method used to obtain the crystals. Suitable recrystallation solvents include ethyl acetate, dioxane, tetrahydrofuran, alcohols (e.g., methanol and ethanol), acetone, acetonitrile, chlorinated solvents (e.g., dichloromethane and chloroform), aromatic solvents (e.g., benzene and toluene), hydrocarbons (e.g., hexane) or mixtures of two or more of the above solvents. Noncentrosymmetric crystals may also be obtained from the melt.

The nonlinear optical device of the invention comprises means to direct at least one incident beam of electromagnetic radiation into an optical element having nonlinear optical properties whereby electromagnetic radiation emerging from said element contains at least one frequency different from the frequency of any incident beam of radiation, said different frequency being an even multiple of the frequency of one incident beam of electromagnetic radiation; said optical element comprising a crystalline compound which is crystallized in a noncentrosymmetric space group, said compound being a nitrostilbene having the general formula given previously and being preferably from the group given previously.

Preferably, the emerging radiation of a different frequency is doubled (second order) (SHG). Preferably, the electromagnetic radiation is radiation from one of a number of common lasers, such as Nd-YAG, Raman-shifted Nd-YAG, semiconductor diode, and Ar or Kr ion.

An optical element is oriented in one of a potentially infinite number of crystal orientations which achieve partially maximized SHG conversion by virtue of phase matching. The specific orientation is chosen for reasons of noncriticality, maximum nonlinearity, increased angular acceptance, etc. Polarized light of wavelength 1.06 $\mu$ from a Nd-YAG laser is incident on the optical element along the optical path. A lens focuses the light into the optical element, light emerging from the optical element is collimated similar lens and passed through a filter adapted to remove light of wavelength 1.06 $\mu$ while passing light of wavelength 0.53 $\mu$.

The optical element is preferably a single crystal having at least one dimension of about 0.5 mm or greater but can be substantially smaller crystals imbedded in a film of polymer or in glass. The smaller crystals can be randomly oriented or aligned with the same orientation, and are preferably aligned. For the smaller crystals, if their size is small enough to prevent light scattering, they can be dispersed in the polymeric binder and pressed, molded or shaped into an optically clear element capable of SHG. The polymer binder should be chosen to be a non-solvent for the aromatic compound. For larger crystallites, similar elements can be prepared if the binder used has an index of refraction matched to the complex, so as to prevent light scatter yet remain transparent.

It will be further apparent to those skilled in the art that the optical elements of the invention are useful in other devices utilizing their nonlinear properties, such as sum and difference frequency mixing, parametric oscillation and amplification, and devices utilizing the electro-optic effect. The use of crystals having nonlinear optical properties in optical devices is also disclosed in U.S. Pat. Nos. 3,747,022, 3,328,723, 3,262,058 and 3,949,323.

The electro-optic modulator of the invention comprises means to direct a coherent beam into an optical element, and means to apply an electric field to said element in a direction to modify the transmission property of said beam, said optical element meeting the description given above for the optical element for the nonlinear optical device of the invention. The preferred optical elements for the nonlinear optical device and electro-optic modulator of the invention are those embodiments set forth earlier herein for the nonlinear optical element.

An electro-optic modulator embodying the invention utilizes an optical element. A pair of electrodes and is attached to the upper and lower surfaces of the element, across which a modulating electric field is applied from a conventional voltage source. The optical element is placed between two polarizers. A light beam such as that from a Nd-YAG laser, is polarized by polarizer focused on the optical element propagated through the crystal or crystals and subjected to modulation by the electric field. The modulated light beam is led out through an analyzer polarizer. Linearly polarized light traversing the optical element is rendered elliptically polarized by action of the applied modulating voltage. A polarizer renders the polarization linear again. Application of the modulating voltage alters the birefringence of the optical element and consequently the ellipticity impressed on the beam. The polarizer then passes a greater or lesser fraction of the light beam as more or less of the elliptically polarized light projects onto its nonblocking polarization direction.

It is understood that the invention has been described with reference to preferred embodiments thereof and that variations are to be included within the scope of the invention. Furthermore, frequency or phase modulation of the light beam by the modulator is possible, although the embodiment specifically described performs intensity modulation.

The invention is further illustrated by the following examples. Unless otherwise stated, all reactions were conducted under nitrogen. SHG was measured by the powder method of Kurtz, et al., J. Appl. Phys., Vol. 39, 3798 (1968), using a Nd-YAG laser ($\omega$=1.064 $\mu$m) and urea as a reference. The polycrystalline urea powder used as a reference had an average particle size of 90 $\mu$m to 125 $\mu$m. The intensity of the second harmonic radiation generated by each sample tested was thus measured relative to that provided by urea.

EXAMPLE 1

1-Cyano-1-(4-Nitrophenyl)-2-(4-Methoxyphenyl)ethylene

A solution of anisaldehyde (138 g, 1.00 mole) and 4-nitrophenyl-acetonitrile (162 g, 1.00 mole) in methanol (2500 mL) was stirred at ambient temperature in a 3 L round-bottom flask fitted with a mechanical stirrer, a condenser and a thermometer. Sodium methoxide (5.4 g, 0.10 mole) was added to this solution, causing a rapid reaction. The solution turned purple, a solid began to deposit and the temperature of the mixture rose slowly. After 4 h, the temperature of the reaction mixture had returned to ambient, and the flask was thick with a fine yellow precipitate. This precipitate was collected by filtration, washed with methanol, then with two 1 L portions of water and dried. The crude product, a bright lemon-yellow powder (276 g), was recrystallized from ethyl acetate at a charge of 50 g/1.1 L to form fine yellow needles (177.7 g, 63%), m.p. 163.9°–164.1° C.

Anal.: Calcd. for $C_{16}H_{12}N_2O_3$: C, 68.57; H, 4.32; N, 9.99. Found: C, 67.94, 68.19; H, 4.32, 4.10; N, 9.67, 9.88. The ir and nmr spectra are consistent with the assigned structure.

Samples of this compound were prepared for SHG measurements by recrystallization from the melt or from one of several solvent systems (ethyl acetate, dioxane, THF, toluene, ethyl acetate/dioxane or THF/dioxane). SHG results for the materials prepared in this Example are presented in the Table.

EXAMPLE 2

1-Cyano-1-(4-Methoxyphenyl)-2-(4-nitrophenyl)ethylene

The title compound in this Example was synthesized according to a procedure disclosed by Zupancic et al. [Synthesis, 913–915 (1981)] for the preparation of α-(4-methoxyphenyl)-β-phenylacrylonitrile. PEG(E)-400 is the dimethyl ether of a linear oligo-polyethylene glycol (average M.W.=400), and is commercially available (Aldrich, Cat. No. 20,239-8).

4-Methoxyphenylacetonitrile (7.63 g, 50 mmol) in toluene (30 mL), PEG(E)-400 (4 g, 10 mmol) and 52% aqueous sodium hydroxide (10.73 g in 12.4 mL water) were placed in a flask equipped with a magnetic stirrer. 4-Nitrobenzaldehyde (7.56 g, 50 mmol) in a minimum of toluene was added dropwise. The mixture was stirred for 1 h at 20° C. and then diluted with water (30 mL). The organic layer was separated, washed with water (3×40 mL) and dried with sodium sulfate. The solvent was removed under reduced pressure and the residue was recrystallized from toluene at −20° C. to give 1-cyano-1-(4-methoxyphenyl)-2-(4-nitrophenyl)ethylene (yield=0.913 g, 6.5%).

SHG results for this compound are presented in the Table.

EXAMPLE 3

1-Methyl-1(4-Nitrophenyl)-2-(4-Methoxyphenyl)ethylene

NaH (0.085 g, 1.77 mmole, 50% in oil dispersion) was added to glyme (10 mL), followed by the addition of methanol (0.071 g, 2.22 mmole). The mixture was stirred for 5 min, and then $(EtO)_2P(O)CH(CH_3)C_6H_4NO_2$—p (0.50 g, 1.74 mmole) in 2 mL of glyme was added dropwise. The mixture was stirred for 1 h and then p-anisaldehyde (0.24 g, 1.76 mmole) was added. The mixture was stirred for 2 days. Saturated ammonium chloride solution was added and the mixture extracted with ether (3×100 mL). The organic layer was dried over $Na_2SO_4$—$K_2CO_3$ and then the solvent removed by rotary evaporation. The residue was chromatographed on silica gel eluted with toluene to give 0.187 g (40%) of 1-methyl-1-(4-nitrophenyl)-2-(4-methoxyphenyl)ethylene.

Samples of this compound were prepared for SHG measurements by recrystallization from ethyl acetate and from toluene. SHG results for this compound are presented in the Table.

EXAMPLE 4

1-Cyano-1-(4-Chlorophenyl)-2-(4-Nitrophenyl)ethylene

4-Nitrobenzaldehyde (2.0 g) was added to a solution of sodium (0.03 g) in methanol (100 mL) to give a yellow solution 4-Chlorobenzyl cyanide (2.0 g) in methanol was added and the resulting solution was stirred for 10 min. The precipitate which formed was filtered, washed with pentane and vacuum-dried to give a light-yellow solid. A second crop of product was obtained by stirring the filtrate for an additional 2–3 days, filtering the solid which formed, washing it with pentane and drying it under vacuum. Total yield: 3.274 g.

Samples of this compound were prepared for SHG measurements by recrystallization from methanol, toluene, ethyl acetate and dichloromethane. SHG results for this compound are presented in the Table.

EXAMPLE 5

1-Cyano-1-(4-Bromophenyl)-2-(4-Nitrophenyl)ethylene

The procedure described in Example 11 was repeated using 4-bromobenzyl cyanide (2.6 g) in place of 4-chlorobenzyl cyanide. The product was a yellow solid (3.111 g).

Samples of this compound were prepared for SHG measurements by recrystallization from chloroform/hexane, toluene/hexane, ethyl acetate/hexane and acetonitrile. SHG results for this compound are presented in the Table.

EXAMPLE 6

1-Cyano-1-(Nitrophenyl)-2-(4-Bromophenyl)ethylene

A solution of sodium (0.03 g) in methanol (100 mL) was added dropwise to a solution of 4-bromobenzaldehyde (2.3 g) and 4-nitrobenzyl cyanide (2.0 g) in methanol (100 mL). The resulting solution was initially purple. After 15 min., the reaction mixture contained an off-white solid and a colorless solution. The solid was isolated by filtration, washed with pentane and vacuum-dried to give a very light yellow solid (0.920 g). A second crop (2.526 g) was obtained by stirring the filtrate overnight and isolating the solid formed.

Samples of this compound were prepared for SHG measurements by recrystallization from toluene, acetonitrile, acetone, chloroform and ethyl acetate. SHG results for this compound are presented in the Table.

EXAMPLE 7

1-Bromo-1-(4-Nitrophenyl)-2-(4-Bromophenyl)ethylene

Diethyl p-nitrobenzylphosphonate (2.73 g) was added to a solution of sodium (0.23 g) in ethanol (10 mL). The reaction mixture was cooled to 0° C. and then bromine (1.60 g) was added. The reaction mixture was stirred for 5 min, filtered and cooled with ice. 4-Bromobenzaldehyde (1.85 g) in ethanol (10 mL) was added, followed by the dropwise addition of sodium (0.23 g) in ethanol (10 mL). More ethanol was added to facilitate stirring the reaction mixture. The mixture was stirred for 1 h and then filtered. The isolated solid was washed with ethanol and vacuum-dried to give a yellow product (2.526 g).

Samples of this compound were prepared for SHG measurements by recrystallization from chloroform/pentane and methanol, or used without recrystallization. SHG results for this compound are presented in the Table.

EXAMPLE 8

1-Bromo-1-(4-Nitrophenyl)-2-(4-Methoxyphenyl)ethylene

The procedure described in example 7 was repeated, except that p-anisaldehyde (1.36 g) was used in place of 4-bromobenzaldehyde. Also, the final reaction mixture was allowed to stir for 2-3 days instead of 1 h. The product isolated was a yellow solid (1.885 g).

Samples of this compound were prepared for SHG measurements by recrystallization from methanol, or used without recrystallization. SHG results for this compound are presented in the Table.

TABLE

SHG DATA FOR STILBENE DERIVATIVES USED IN EXAMPLES 1-8

| Example | SHG, relative to urea | Crystal Growing Medium |
|---|---|---|
| 1 | 180-300 | Ethyl acetate |
|   | 0.15-0.17 | Dioxane |
|   | 4 | THF |
|   | 0.4 (emissive) | Ethyl acetate/dioxane |
|   | 0.5 (emissive) | THF/dioxane |
|   | 90 | Melt |
|   | 250 | Toluene |
| 2 | 0.1 (emissive) | Toluene |
| 3 | 0.4 | Ethyl acetate, −20° C. |
|   | 0.2 | Toluene, −20° C. |
| 4 | 0.5 | Methanol |
|   | 0.5 | Toluene |
|   | 0.25 | Ethyl acetate |
|   | 0.25 | Dichloromethane |
| 5 | 0.1 | Chloroform/hexane |
|   | 0.4 | Toluene/hexane |
|   | 0.24 | Ethyl acetate/hexane |
|   | 0.08 | Acetonitrile |
| 6 | 19 | Toluene |
|   | 22 | Acetonitrile |
|   | 23 | Acetone |
|   | 27 | Chloroform |
|   | 18 | Ethyl acetate |
| 7 | 11 | (Not recrystallized) |
|   | 93 | Chloroform/pentane |
|   | 77 | Methanol |
| 8 | 37 | (Not recrystallized) |
|   | 168 | Methanol |

What is claimed is:

1. A nonlinear optical device capable of second harmonic generation comprising a nonlinear optical element, a source of coherent optical radiation, and means to direct the coherent beam of radiation into the nonlinear optical element, said nonlinear optical element comprising a compound having the general formula

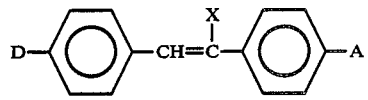

wherein A or D is $NO_2$ and, correspondingly,

D or A is selected from the group consisting of F, Cl, Br, I, CHO and OR where R is selected from the group consisting of H, $C_1$–$C_{10}$ branched or unbranched alkyl, and $C_1$–$C_{10}$ branched or unbranched hydroxyalkyl, and X is selected from the group consisting of F, Cl, Br, I, CN, $C_1$–$C_4$ branched or unbranched alkyl;

said compound being crystallized in a noncentrosymmetric space group, provided when X is CN, then (1) A is selected from the group consisting of CHO and OR and D is $NO_2$ or (2) D is selected from the group consisting of CHO and OR and A is $NO_2$.

2. An optical element as defined in claim 1 where R in the compound of said element, wherein D or A is OR, is methyl.

3. The nonlinear optical device as defined in claim 1 wherein the compound is 1-cyano-1-(4-nitrophenyl)-2-(4-methoxyphenyl)ethylene.

4. An optical element as defined in claim 1 wherein the compound is 1-cyano-1-(4-methoxyphenyl)-2-(4-nitrophenyl)ethylene.

5. An optical element as defined in claim 1 wherein the compound is 1-methyl-1-(4-nitrophenyl)-2-(4-methoxyphenyl)ethylene.

6. An optical element as defined in claim 1 wherein the compound is 1-bromo-1-(4-nitrophenyl)-2-(4-bromophenyl)ethylene.

7. An optical element as defined in claim 1 wherein the compound is 1-bromo-1-(4-nitrophenyl)-2-(4-methoxyphenyl)ethylene.

8. In an electro-optic modulator comprising means to direct a coherent beam of radiation into an optical element and means to apply an electric field to said optical element in a direction to modify the transmission of said beam, the improvement wherein said beam is directed into the optical element defined in claim 1.

* * * * *